(12) United States Patent
Parker

(10) Patent No.: US 7,172,557 B1
(45) Date of Patent: Feb. 6, 2007

(54) SPIROMETER, DISPLAY AND METHOD

(75) Inventor: Frederick A. Parker, Gwynedd Valley, PA (US)

(73) Assignee: Caldyne, Inc., Gwynedd Valley, PA (US)

(*) Notice: Subject to any disclaimer, the term of this patent is extended or adjusted under 35 U.S.C. 154(b) by 432 days.

(21) Appl. No.: 10/651,241

(22) Filed: Aug. 29, 2003

(51) Int. Cl.
*A61B 5/00* (2006.01)

(52) U.S. Cl. ............... 600/529; 600/533; 128/200.24; 128/204.25

(58) Field of Classification Search ............... 600/532, 600/529, 538, 533; 128/204.25, 200.24, 128/205.23
See application file for complete search history.

(56) References Cited

U.S. PATENT DOCUMENTS

| | | | | |
|---|---|---|---|---|
| 3,081,766 A | * | 3/1963 | Felkel et al. | 600/538 |
| 4,440,177 A | * | 4/1984 | Anderson et al. | 600/532 |
| 4,774,941 A | * | 10/1988 | Cook | 128/205.13 |
| 4,884,460 A | * | 12/1989 | Nowacki et al. | 73/861.52 |
| 4,914,720 A | * | 4/1990 | Knodle et al. | 250/343 |
| 5,038,621 A | * | 8/1991 | Stupecky | 73/861.53 |
| 5,137,026 A | * | 8/1992 | Waterson et al. | 600/538 |
| 5,518,002 A | * | 5/1996 | Wolf et al. | 600/538 |
| 5,592,934 A | | 1/1997 | Thwaites | 128/203.12 |
| 5,743,270 A | | 4/1998 | Gazzara et al. | 128/724 |
| 5,789,660 A | | 8/1998 | Kofoed et al. | 73/23.2 |
| 5,997,483 A | | 12/1999 | Johnson | 600/538 |
| 6,090,049 A | * | 7/2000 | Cha | 600/538 |
| 6,128,963 A | | 10/2000 | Brömster | 73/861.52 |
| 6,159,147 A | * | 12/2000 | Lichter et al. | 600/300 |
| 6,322,519 B1 | * | 11/2001 | Moulin | 600/538 |
| 6,435,183 B1 | * | 8/2002 | Farman | 128/204.25 |
| 6,502,573 B1 | * | 1/2003 | Ratner | 128/207.17 |
| 6,543,449 B1 | * | 4/2003 | Woodring et al. | 128/204.18 |

OTHER PUBLICATIONS

Internet Print-Out: www.capnography.com—Site updated Apr. 2003, 3 sheets.
Sales Catalog sheet—"Lifesaver® Reusable Resuscitators".
Sales Catalog sheet—"Lifesaver® Disposable Resuscitators".

* cited by examiner

*Primary Examiner*—Charles A. Marmor, II
*Assistant Examiner*—Karen E Toth
(74) *Attorney, Agent, or Firm*—Jim Zegeer

(57) ABSTRACT

A spirometer coupled to a manual resuscitator. An air tube in the spirometer has a converging section, a laminar flow section and a pressure recovery section. A microcontroller and a display of expiratory flow parameters is provided.

13 Claims, 4 Drawing Sheets

SPIROMETER, DISPLAY AND METHOD

The present invention relates to spirometers and more particularly to spirometers which are coupled to manual resuscitators. The invention also relates to spirometers which optionally include carbon dioxide ($CO_2$) sensors and/or carbon monoxide (CO) sensors.

BACKGROUND OF THE INVENTION

Millions of adult manual resuscitators are used each year in emergency situations to temporarily augment ventilation, both inside and outside of hospitals. These devices are sometimes used by personnel with limited training, as has been pointed out in the introduction to ISO8382; the International Standard that specifies the minimum performance and safety requirements for the type of resuscitator with which our spirometer is intended to be used.

Because of the limited training of some of the clinicians which may use these resuscitators, and the importance of their providing correct ventilatory parameters (tidal and minute volumes) in critical situations, we believe the use of the spirometer to be of great importance as it will give the clinician a good indication of the amount of gas the patient is actually receiving by measuring the amount of gas the patient is exhaling. However, the value of the spirometer extends beyond this and can provide valuable information to even a well-trained clinician. For example, the clinician may assume that the patient is receiving the amount of gas determined by the frequency and amount of compression applied to the bag. Under ideal conditions this is true, but particularly when the patient's lungs are non-compliant or a mucous plug is present, leakage can occur. Potential sites of leakage are around the face mask or endotracheal tube cuff, or through a pressure vent valve, at tubing connections, through a malfunctioning air inlet valve, and elsewhere. In reality, the patient may be receiving little or no ventilation. The instructions typically supplied by the manufacturers of the manual resuscitators, for the clinician to observe the rise and fall of the chest and listen for exhalation to assure proper ventilization, is often not practical, especially at prehospital emergency sites. Factors such as high background noise and difficulty in seeing chest wall movement due to rigid chest walls, obesity and bulky clothing can render these instructions meaningless. This has been frequently pointed out in the literature.

Furthermore, ISO 8382 recommends that a functional test of the resuscitator be carried out immediately prior to use. This is indeed a good idea but often overlooked when a patient needs immediate intervention to initiate respiration.

BRIEF DESCRIPTION OF THE INVENTION

Spirometers are devices used to measure the volume and flow rate of gas exhaled and/or inhaled by a user or patient. The information displayed by the spirometer addresses the problems outlined above by giving the clinician the needed feedback as to how well the resuscitator is functioning and whether or not the desired ventilation parameters are being achieved.

The present invention provides a spirometer having a housing and an exhale air tube. The exhale air tube includes a first section, a contiguous second section and a third section. The first section has a converging channel in which the exhaled air/gas velocity is increased thereby diminishing static pressure. The second section has a laminar air flow pressure drop.

A pressure transducer connected to measure the pressure drop across the first and second sections provides an indication of the pressure drop across the two sections. The third section of the exhale air tube has a gradually diverging flow diameter to act as a pressure recovery diffuser. A feature of the invention is that the air tube has an adaptor coupling member for easily coupling the spirometer to the manual resuscitator. The gas inlet of the adapter has complementary conical dimensions to the conical expiratory port of the manual resuscitator.

Advantageously, optional $CO_2$ and/or CO sensors may be included in the instrument. From the pressure transducer voltage output, the instrument derives and displays the expiratory flow, expiratory tidal volume, expiratory minute volumes and ventilator frequency. In addition, the exhaled $CO_2$ and/or CO levels are displayed giving additional valuable information to the clinician, as will be discussed in more detail below.

DESCRIPTION OF THE DRAWINGS

The above and other objects, advantages and features of the invention will become more apparent when considered with the accompanying drawings wherein.

DETAILED DESCRIPTION OF THE INVENTION

Figure 1:
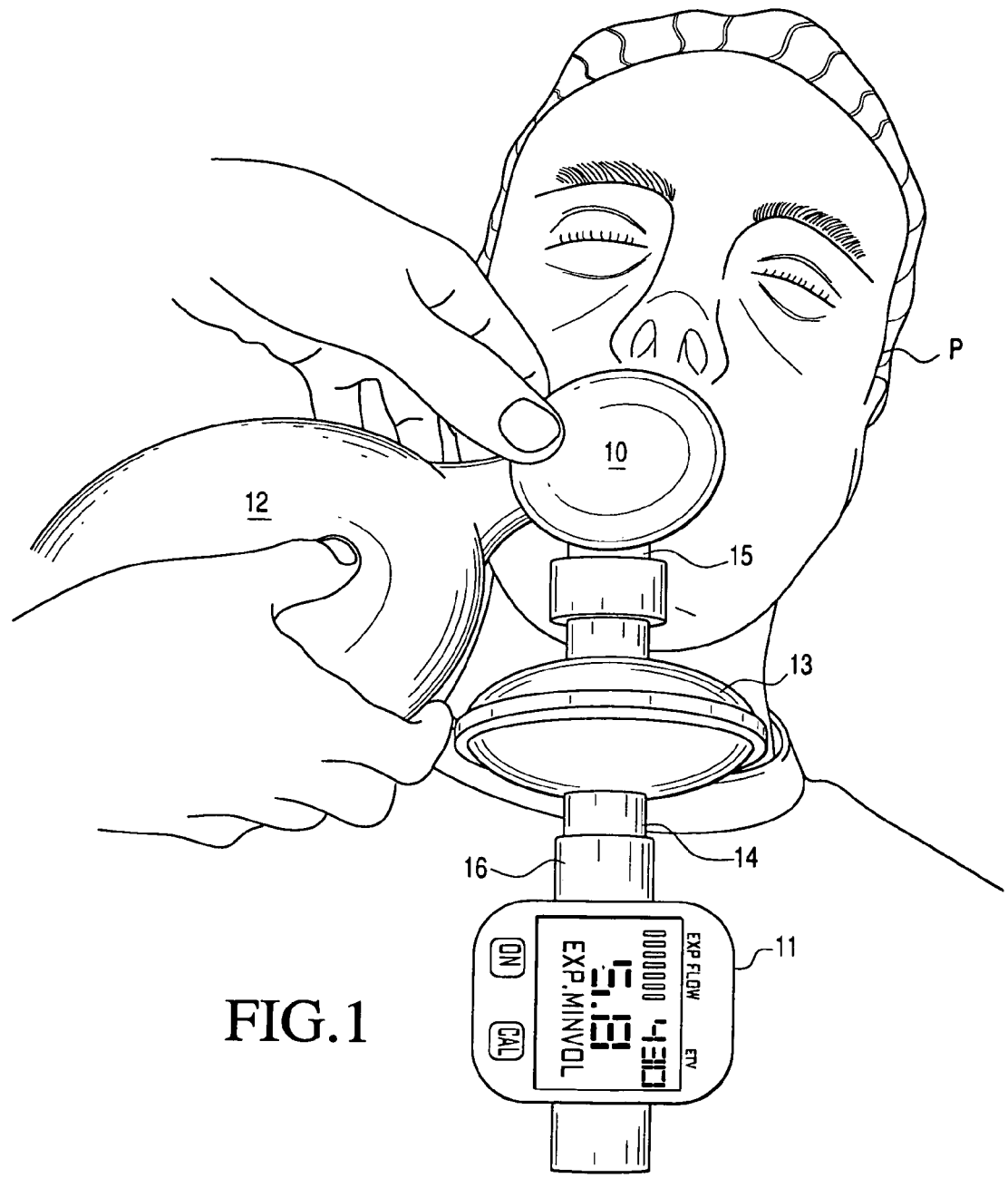
FIG. 1 is a plan view of a patient being ventilated with a manual resuscitator, with the spirometer attachment on the exhaust side of the resuscitator.

Referring to FIG. 1, the patient P is shown having a manual resuscitator 10 applied thereto with the spirometer 11 of the present invention mounted or attached to an optional filter 13 which is mounted thereto. The manual resuscitator 10 is conventional and includes a squeeze-bag 12, a patient connection means (not shown), which may be either a mask or endotracheal tube, and an exhaust port 15. The exhaust port 15 of the manual resuscitator and the filter discharge port 14 are typically conical tapered male connectors of about 30 millimeters.

Figure 2A:
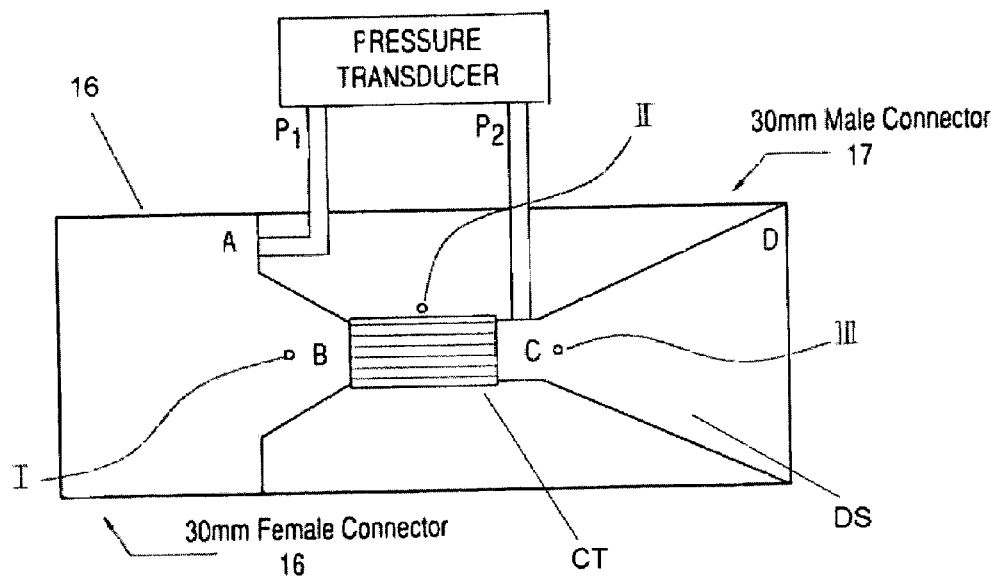
FIG. 2A is a schematic illustration of the flow tube invention showing the combination of the two means of creating the ΔP used to measure flow and the location of the pressure transducer connections.
Figure 2B:
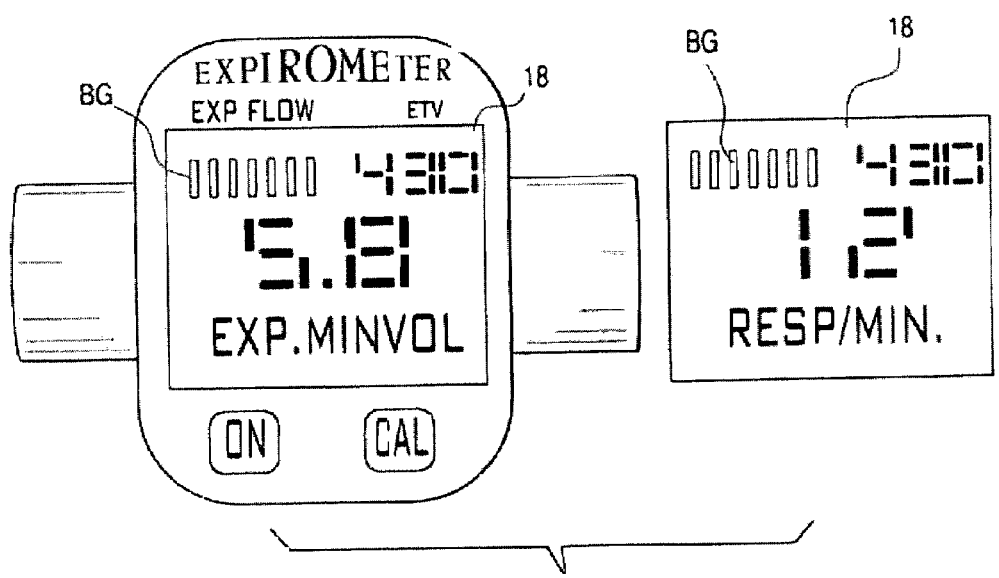
FIG. 2B illustrates two views of the displayed parameters and shows examples of the alternating Expiratory Tidal Volume (ETV) and Respirations per minute (RESP/MIN) values.

Referring to FIG. 2A, a diagrammatic illustration of the exhale flow tube of the spirometer of the present invention includes a female conical connector 16 of about 30 mm diameter so that it can be complementary fitted on exhaust port 15 of the manual resuscitator or on the discharge port 14 of the optional filter, as shown in FIG. 1. The exhale air tube 17 having first, second and third sections I, II and III, respectively, will be described extensively hereinafter. The pressure drop between points A and C is measured by a pressure transducer, and ventilatory parameters are displayed on an LCD display 18 as depicted in FIG. 2B.

Display Arrangement

Expiratory Flow—The flow is displayed graphically, giving the clinician a visual representation of expiratory flow. This can help the clinician avoid initiating the next inspiratory cycle before the patient's lungs empty.

Expiratory Tidal Volume—Each expired breath is displayed in milliliters. The clinician, typically, keys the tidal volume to the patient's size.

Expiratory Minute Volume—This is a predicted volume based on the last several breaths. It is an important parameter as it tells the clinician how much ventilatory gas the patient is receiving over time. The clinician typically will also attempt to key this to the patient's size.

Ventilatory Frequency—The ventilatory frequency is also a calculated value based on the last several breaths. It, along with the average tidal volume, determines the minute volume.

The availability of these data permit the clinician to vary the different ventilation parameters to meet specific patient needs. For example, should the clinician wish to provide a high ventilatory frequency, the tidal volume can be adjusted to obtain the desired minute volume and avoid hyperventilating the patient; and, by observing the expiratory flow, avoid over-inflating the patient's lungs.

Bar graph BG is a visual representation of the expiratory flow, the number of bars energized being a quantitative indication of the instantaneous expiratory flow rate.

The ETV (Expiratory Tidal Volume) display turns on as soon as the EXP FLOW (Expiratory Flow) display goes to zero, following an exhalation. It turns off as soon as the next exhalation flow commences. The volume is presented in milliliters, rounded off to the nearest 10 milliliters.

The EXP MIN VOL (Expiratory Minute Volume) and RESP/MIN (Respirations Per Minute) displays alternate every 2½ seconds with updated information.

Gas Flow Measurement

The means of measuring gas flow is to measure the pressure change ($\Delta P$) across a flow restrictor. Flow restrictors can be designed to impose a pressure drop which is proportional to the density of the gas or to the gas viscosity, or to a combination of the two. The preferred embodiment of the present invention uses a combination of the two.

Preferably, the laminar flow restrictor, which imposes a pressure drop proportional to the viscosity, consists of, in effect, a bundle of capillary tubes CT. In order to design a laminar flow restrictor with workable dimensions, it is desirable to substantially reduce the flow diameter of the restrictor from the flow diameter of the expiratory port of the resuscitator. As the flow diameter is decreased (between A and B of FIG. 2A), the velocity of the gas increases, and, in accordance with the Bernoulli effect, the static pressure decreases. This pressure drop is proportional to the gas density. Therefore, if the pressure to be measured by the pressure transducer is between a point prior to the reduced diameter of the flow path and the point of exit from the reduced diameter of the laminar flow restrictor, a maximum $\Delta P$ signal will be obtained to measure flow. These pressure measurement points are illustrated in FIG. 2A as A and C.

As the $\Delta P$ between the high pressure sensing port P1 (point A) and the entrance to the laminar flow restrictor (point B) is proportional to the flow volume squared, multiplied by the gas density, and the pressure drop between the entrance of the laminar restrictor (point B) and the low pressure sensing port P2 (point C) is linearly proportional to the flow volume multiplied by the viscosity, we get an overall $\Delta P$ which is proportional to the flow volume to something in the order of the 1.5 power of the flow, and a function of both the gas density and viscosity.

The resulting pressure measurements, based on both the density and viscosity have several desirable characteristics. For example, the flow sensor will normally be calibrated with air. However, when used to measure the expiratory flow from a patient, it will normally contain some $CO_2$; perhaps as high as seven percent. The $CO_2$ causes the density of the gas to increase and the viscosity to decrease. Therefore, by combining the two, we essentially negate the error in flow measurement that would otherwise be introduced by the presence of the $CO_2$.

The diffuser section DS (between C and D) is designed to recover a substantial portion of the static pressure drop between. A and B. Therefore, the $\Delta P$ available for measuring the expiratory gas flow is actually greater than the overall pressure drop caused by the spirometer and gives an adequate signal for reliable flow measurements, even at low flows. In order to minimize the degrading effect of moisture on the performance of the laminar flow restrictor II, filter 13 may be provided as illustrated in FIG. 1, which may also protect the instrument and the clinician from contamination by pathogens exhaled by the patient.

In summary, the $\Delta P$ measured by the pressure transducer is a function of the expiratory gas flow rate. The voltage produced by the pressure transducer versus time is used to calculate all of the displayed expiratory parameters.

Figure 3:
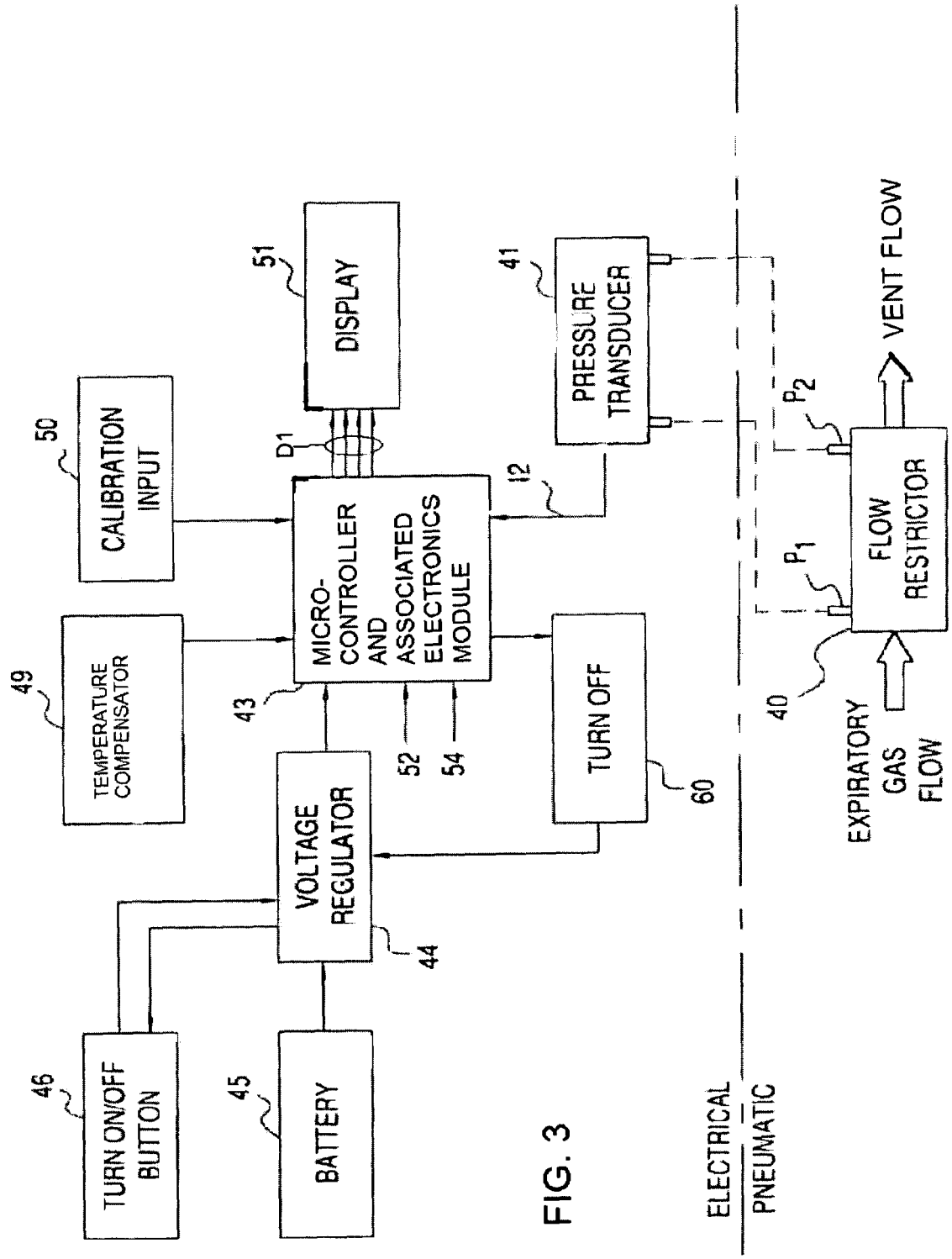
FIG. 3 is a block diagram of the electrical components connected to the pressure transducer and also shows optional inputs from the $CO_2$ and/or CO sensors.

Referring now to the block diagram of FIG. 3, the flow restrictor shown in FIGS. 2A and 2B is designated generally as element 40 in FIG. 3 and shows the expiratory gas flow and vent flow. Pressure transducer ports P1 and P2 are shown as connected by dotted lines to the pressure transducer 41 which transduces the pressure differential betweens points A and C to a signal voltage. Pressure transducer 41 provides an output signal voltage on line 42 to microcontroller and associated display electronics module 43. The microcontroller 43 is supplied with power from voltage regulator 44 which is coupled to battery 45 by turn-on and turn-off button 46. The microcontroller 43 receives a temperature compensation input from compensator 49 (which may be a thermistor) and a calibration voltage input from calibration input module 50. The display 51, preferably an LCD electrical display, receives display inputs DI from the microcontroller 43. $CO_2$ voltage signals from an optional $CO_2$ sensor are supplied on line 52 to microcontroller 43, and a similar signal voltage from a CO sensor is supplied to the microcontroller 43 on line 54. An automatic turn-off signal generated inside the microcontroller senses the non-use of the unit for a given period DS time, say 5 or 10 minutes, and turns the power off.

Figure 4A:
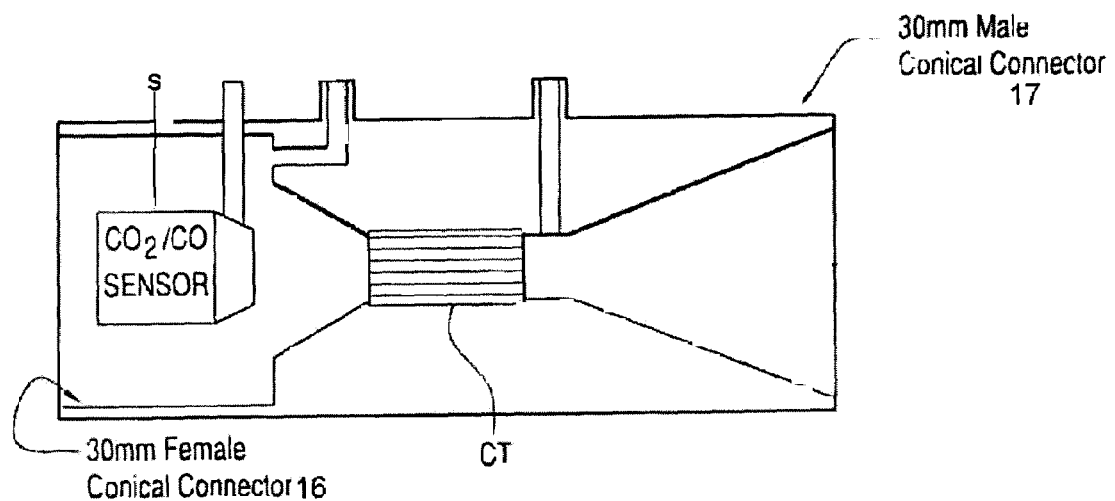
FIG. 4A is a schematic illustration of the spirometer flow tube with an optional $CO_2$ (or CO) sensor.

In addition to sensing the expiratory gas volume parameters, as already described, one embodiment of the spirometer will contain carbon dioxide ($CO_2$) sensors, as shown in FIG. 4A, to measure end tidal $CO_2$. This measurement is of importance in that it indicates to the clinician whether or not the ventilatory volume being supplied is correct. The value of monitoring the end tidal $CO_2$ is well known in the art.

A further embodiment of the spirometer will contain a carbon monoxide (CO) sensor, located where the $CO_2$ sensor is shown in FIG. 4A. Measuring CO is of value in that it is important for the clinician, early on, to know whether a patient has been poisoned by CO so that the appropriate treatment can be initiated. Timely treatment can help prevent severe long-term neurological damage. See the article, The Silent Killer, from the January 2003 edition of JEMS.

Ventilation with a high level of oxygen, by means of the manual resuscitator, in addition to being an important medical treatment, can enhance the ability of the spirometer CO sensor to detect possible CO poisoning. The elevated inspired $O_2$ level helps the patient eliminate CO, resulting in a higher level of CO in the exhaled breath, making it more easily measured. The CO sensor therefore enhances the value of the spirometer by making it an important and effective diagnostic tool, in addition to its value in monitoring respiratory parameters. As before (see FIG. 2A), the inlet and outlet connectors of the spirometer containing a $CO_2$ and/or CO sensor are standard 30 mm connectors, as shown in FIG. 4A. The inlet connector 16 is female and the outlet 17 is male. This permits the spirometer to mate directly to the manual resuscitator expiratory port and also permits devices, such as a PEEP valve, designed to fit the manual resuscitator expiratory port, to fit directly to the spirometer expiratory port.

The dimensions for the standard tapered 30 mm conical connectors are specified in ISO535601 and their use with the manual resuscitator, with which the spirometer is intended to be used, is specified in ISO 8382.

Figure 4B:
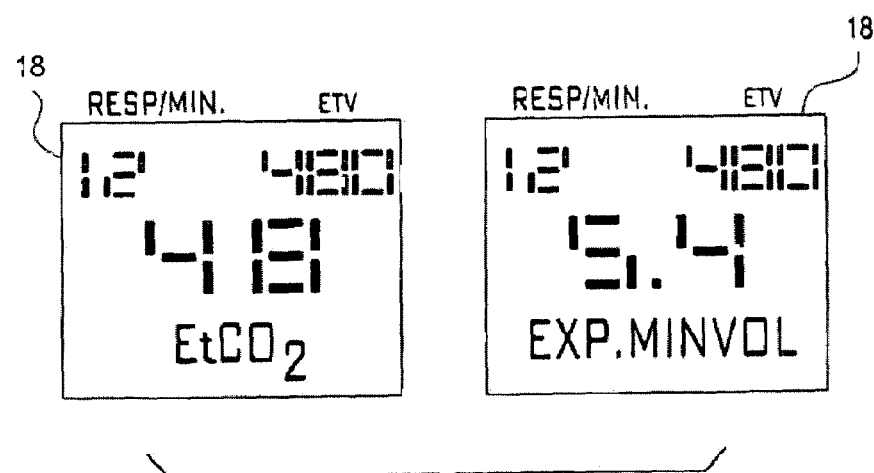
FIG. 4B shows the displays when the $CO_2$ (or CO) sensor is included.

If a $CO_2$ or CO sensor is incorporated in the spirometer, the displays will be modified. FIG. 4B shows one possible arrangement. The large numbers ($EtCO_2$ and EXP.MIN. VOL) would alternate every 2½ seconds. The display is shown for the $EtCO_2$ version. For the CO version, the display would read "$CO_{ppm}$".

While the invention has been described in relation to preferred embodiments of the invention, it will be appreciated that other embodiments, adaptations and modifications of the invention will be apparent to those skilled in the art.

What is claimed is:

1. A spirometer comprising a housing,
   an exhale air tube in said housing, said exhale air tube including a first section and a contiguous second section, said first section having a converging channel in which flow velocity is increased thereby decreasing the static pressure and said second section having laminar flow air pressure drop, and
   a pressure transducer connected to measure the pressure drop across said first and second sections and providing an indication of the pressure drop.

2. The invention defined in claim 1 including a gas inlet port coupling member for coupling said spirometer to a manual resuscitator.

3. The invention defined in claim 1 including a gas outlet port of the same dimensions as the expiratory port of a manual resuscitator.

4. The invention defined in claim 1 having a contiguous third section, said third section having a gradually divergent flow diameter to act as a static pressure recovery diffuser.

5. The invention defined in claim 1 including a $CO_2$ sensor for producing electrical signals corresponding to $CO_2$ gas in expiratory gas and a display means connected to said sensor for displaying said $CO_2$ gas level in said expiratory gas.

6. The invention defined in claim 1 including a CO gas sensor means for sensing CO in expiratory gases and producing an electrical signal corresponding thereto and display means connected to said sensing means for displaying said CO gas level in said expiratory gas.

7. The invention defined in claim 1 including a microcontroller connected to said pressure transducer and a display device connected to said microcontroller for providing a graphical display of expiratory flow.

8. The invention defined in claim 1 including a microcontroller connected to said pressure transducer, a display device connected to said microcontroller wherein said microcontroller computes the expiratory minute volume, expiratory tidal volume and the expiratory ventilatory frequency from said indication of pressure drop and displays same on said display device.

9. A resuscitator system comprising in combination:
   a manual resuscitator having a squeeze-bag, means for coupling respiratory gases from said squeeze-bag to a patient and receiving expiratory gas from said patient, an expiratory exhaust gas port coupled to said patient, and
   a spirometer comprising a housing,
   an exhale air tube in said housing, said exhale air tube including a first section and a contiguous second section, said first section having a converging channel in which flow velocity is increased thereby decreasing the static pressure and said second section having laminar flow air pressure drop, and
   a pressure transducer connected to measure the pressure drop across said first and second sections and providing an indication of the pressure drop coupled to said expiratory exhaust gas port, said spirometer including a microcontroller connected to said pressure transducer, a display device connected to said microcontroller for presenting to the user patient expiratory parameters including expiratory tidal volume, and expiratory minute volume and expiratory ventilatory frequency.

10. The resuscitator system defined in claim 9 wherein said display device includes a graphical display of expiratory flow.

11. The resuscitator system defined in claim 9 wherein said spirometer includes a $CO_2$ sensor for producing an electrical signal corresponding to $CO_2$ gas in said expiratory gas and means coupled to said display for displaying to said user the $CO_2$ level in said expiratory gas.

12. The resuscitator system defined in claim 9 including means for sensing CO gas in said expiratory gases and producing an electrical signal corresponding thereto, and means for coupling said electrical signal to said display for displaying on said display monitor the level of CO gas in said expiratory gas.

13. The resuscitator system defined in claim 9 wherein said spirometer includes sensor means for sensing both the level of CO gas and the level of $CO_2$ gas in said expiratory gases and producing electrical signals corresponding thereto, and means for converting said electrical signal for displaying said CO and $CO_2$ levels on said display monitor.

* * * * *